US011235296B2

(12) United States Patent
Jakob et al.

(10) Patent No.: US 11,235,296 B2
(45) Date of Patent: Feb. 1, 2022

(54) METHOD AND DEVICE OF MAKING A SUSPENSION OF MICROPARTICLES HOMOGENEOUSLY DISTRIBUTED IN AN AQUEOUS LIQUID CARRIER

(71) Applicant: Bracco Suisse SA, Manno (CH)

(72) Inventors: Laurent Jakob, Plan-les-Ouates (CH); Frédéric Rivas, Plan-les-Ouates (CH)

(73) Assignee: Bracco Suisse SA, Plan-les-Ouates (CH)

( * ) Notice: Subject to any disclaimer, the term of this patent is extended or adjusted under 35 U.S.C. 154(b) by 756 days.

(21) Appl. No.: 16/063,043

(22) PCT Filed: Dec. 21, 2016

(86) PCT No.: PCT/EP2016/082071
§ 371 (c)(1),
(2) Date: Jun. 15, 2018

(87) PCT Pub. No.: WO2017/114706
PCT Pub. Date: Jul. 6, 2017

(65) Prior Publication Data
US 2018/0361331 A1     Dec. 20, 2018

(30) Foreign Application Priority Data

Dec. 29, 2015  (EP) .................................... 15203007

(51) Int. Cl.
*B01F 11/00*   (2006.01)
*B01F 13/00*   (2006.01)
(Continued)

(52) U.S. Cl.
CPC ...... *B01F 11/0002* (2013.01); *B01F 11/0017* (2013.01); *B01F 11/0097* (2013.01);
(Continued)

(58) Field of Classification Search
CPC .......... B01F 11/0002; B01F 2215/0034; B01F 11/0017; A61M 5/1456
See application file for complete search history.

(56) References Cited

U.S. PATENT DOCUMENTS

| 6,431,745 B1* | 8/2002 | Schlumberger ........... B01F 9/10 366/211 |
| 2014/0163366 A1* | 6/2014 | Schneider ........... A61M 5/1456 600/432 |
| 2014/0249412 A1 | 9/2014 | Yamamoto |

FOREIGN PATENT DOCUMENTS

| EP | 1035882 B1 | 6/2004 |
| EP | 1561483 A1 | 8/2005 |

(Continued)

OTHER PUBLICATIONS

International Patent Application No. PCT/EP2016/082071, International Search Report & Written Opinion dated Mar. 3, 2017, 11 pages.

*Primary Examiner* — Elizabeth Insler
(74) *Attorney, Agent, or Firm* — Fredrikson & Byron, P.A.

(57) ABSTRACT

A method of mixing a liquid composition that includes microparticles dispersed in an aqueous liquid carrier may involve a first premixing step and a second premixing step. During the first premixing step a receptacle is oscillated about a longitudinal axis clockwise and counter-clockwise from a first reference point through a first angle of rotation for a first period of time and at a first angular velocity. During the second premixing step the receptacle is oscillated about the longitudinal axis clockwise and counter-clockwise from a second reference point through a second angle of rotation for a second period of time and at a second angular velocity. In examples, the first angle of rotation is smaller (Continued)

than said second angle of rotation, and the first period of time is shorter than the second period of time.

16 Claims, 11 Drawing Sheets

(51) Int. Cl.
*A61M 5/00* (2006.01)
*A61M 5/145* (2006.01)

(52) U.S. Cl.
CPC ......... *B01F 13/0023* (2013.01); *A61M 5/007* (2013.01); *A61M 5/1456* (2013.01); *B01F 2215/0034* (2013.01); *B01F 2215/0454* (2013.01)

(56) References Cited

FOREIGN PATENT DOCUMENTS

| | | | |
|---|---|---|---|
| WO | 2011103384 | A1 | 8/2011 |
| WO | 2013074507 | A2 | 5/2013 |
| WO | 2014135853 | A1 | 9/2014 |

\* cited by examiner

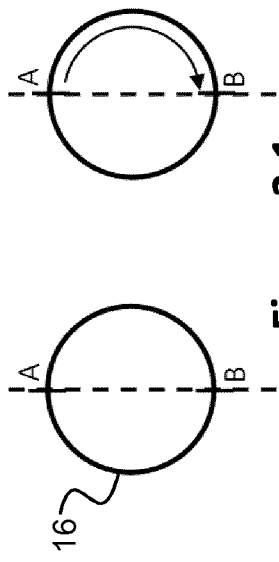
Figure 2.1
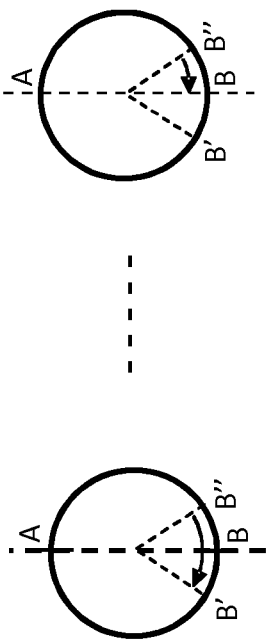
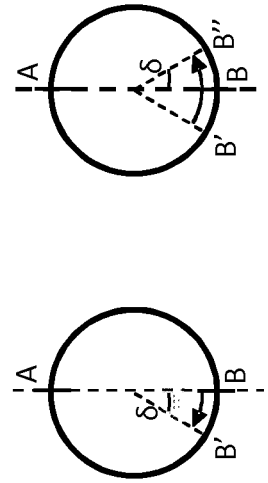
Figure 2.2
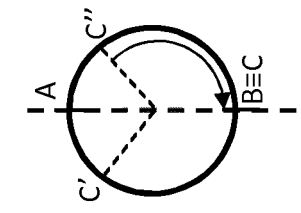
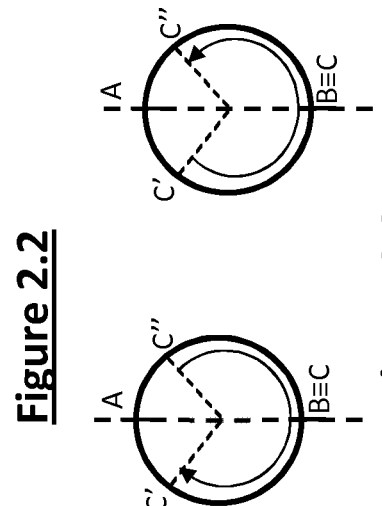
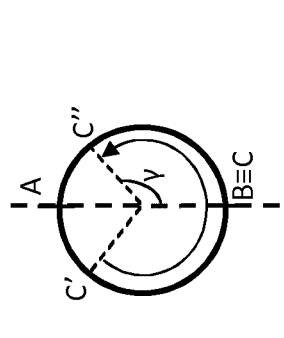
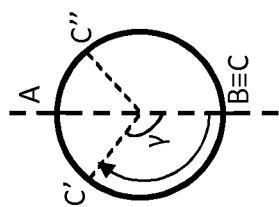
Figure 2.3

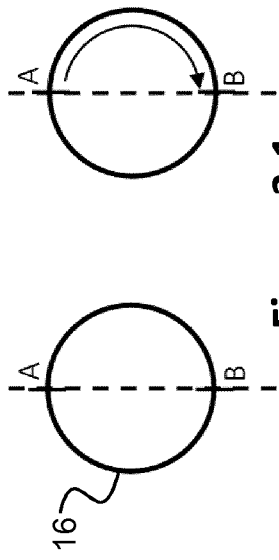
Figure 3.1
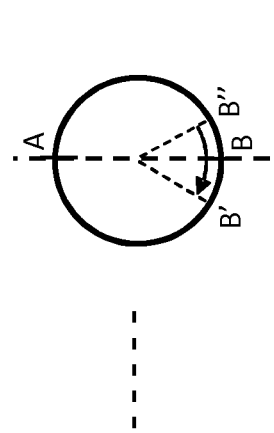
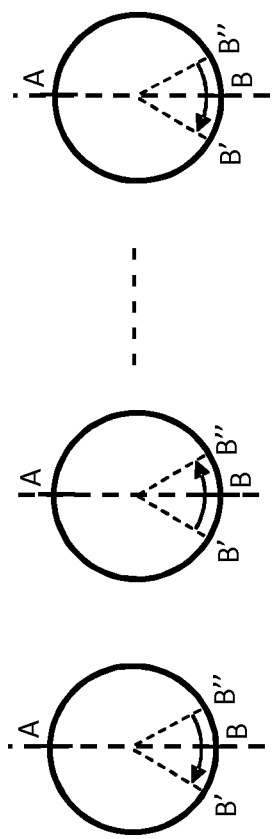
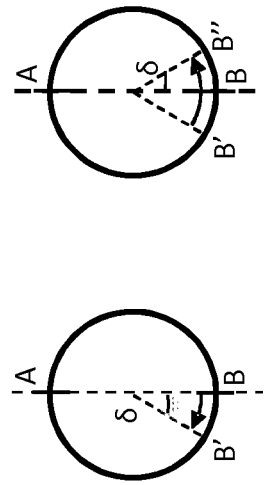
Figure 3.2
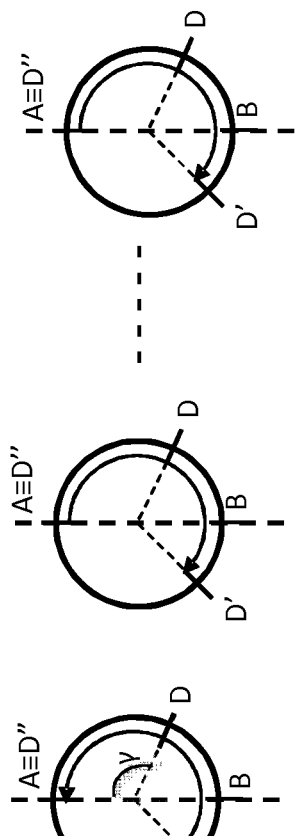
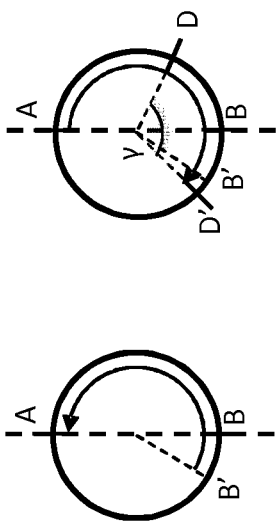
Figure 3.3

METHOD AND DEVICE OF MAKING A SUSPENSION OF MICROPARTICLES HOMOGENEOUSLY DISTRIBUTED IN AN AQUEOUS LIQUID CARRIER

This application is a 35 U.S.C. 371 national stage filing from International Application No. PCT/EP2016/082071, filed Dec. 21, 2016, which claims priority to European Application No. 15203007.8, filed Dec. 29, 2015. The entire contents of both these applications are incorporated herein by reference.

FIELD OF THE INVENTION

The present invention generally relates to the administration by injection or infusion of a liquid composition. The liquid composition can be, for instance, a liquid medicament. Alternatively, the liquid composition can be, for instance, a diagnostically active contrast agent. More in particular, the present invention concerns a method and device of making available in a short period of time a suspension of microparticles homogeneously distributed in a liquid carrier, preferably an aqueous liquid carrier. In one embodiment, the suspension of microparticles homogeneously distributed can be injected or infused to a patient's body, typically a patient's blood vessel that reaches a body portion to be treated, or a patient's body organ to be treated.

STATE OF THE ART

EP 1 035 882 B1 discloses a method of administering to patients by injection or infusion a suspension of microparticles homogeneously distributed in an aqueous liquid carrier by means of an injector system comprising a syringe containing said suspension and a power driven piston for injecting said suspension into a patient. According to the method, the suspension in the syringe is subjected to a rotation or rocking motion, thereby maintaining said suspension homogeneous by preventing segregation of the microparticles by gravity or buoyancy, this being without damaging said particles or disturbing their distribution.

EP 1 561 483 A1 discloses an infusion pump for syringes, comprising a supporting structure, a support for a syringe, which can be rigidly associated with the syringe and can be associated with the supporting structure so that they can rotate alternately about an axis that is substantially perpendicular to the longitudinal axis of the syringe, and a first actuation for actuating the alternating rotation and a second actuation for actuating the sliding of the plunger of the syringe, which cooperate functionally with the first actuation.

SUMMARY OF THE INVENTION

While the apparatus and method of EP 1 035 882 have good performance, the Applicant has further investigated and improved the phase of mixing that is carried out before starting the infusion phase into a patient.

According to the teachings of said patent and practical use thereof, the infusion or injection to a patient takes place after an initial mixing phase which lasts at least about 90 seconds. This initial mixing phase of the liquid composition allows the microparticles present in the liquid composition to be properly and uniformly re-suspended. When this condition is advantageously reached, the injection/infusion phase can be started while the initial mixing phase is still carried out, i.e. the initial mixing phase is not interrupted during the whole injection/infusion phase and it is performed at the same operational conditions which are not varied during the whole mixing and injection/infusion phases.

While the time duration of the initial mixing phase is deemed by the technical operators to be substantially acceptable for obtaining a sufficiently homogeneous suspension before the infusion/injection phase is started, an objective of the present invention is to advantageously reduce this initial mixing time without affecting the homogeneity of the suspension. A further objective of the present invention is not only to advantageously reduce the initial mixing time before the injection/infusion phase is started, but also to improve the homogeneity of the microparticles suspension.

According to the present invention, a premixing phase is envisaged which comprises two premixing steps, i.e. a first premixing step and a second premixing step, during which the receptacle (i.e. a syringe) containing the microparticles suspension is oscillated about the receptacle longitudinal axis according to specific rotational parameters.

According to a first aspect, the present invention provides a method of mixing a liquid composition, wherein said liquid composition comprises microparticles dispersed in an aqueous liquid carrier and wherein said liquid composition is contained in a receptacle having a longitudinal axis, the method comprising:
  a first premixing step in which the receptacle is oscillated about said longitudinal axis clockwise and counter-clockwise from a first reference point through a first angle of rotation for a first period of time and at a first angular velocity;
  a second premixing step in which the receptacle is oscillated about said longitudinal axis clockwise and counter-clockwise from a second reference point through a second angle of rotation for a second period of time and at a second angular velocity; and
  wherein said first angle of rotation is smaller than said second angle of rotation, and said first period of time is shorter than said second period of time.

According to an embodiment of the present invention, the second reference point coincides with the first reference point.

According to an alternative embodiment of the present invention, the second reference point is different from the first reference point.

According to a second aspect, the present invention provides an infusion pump device for mixing a liquid composition, wherein said liquid composition comprises microparticles dispersed in an aqueous liquid carrier and wherein said liquid composition is contained in a receptacle having a barrel, a plunger and a longitudinal axis, wherein the barrel is supported in a rotatable fashion by a cradle arrangement, wherein the plunger is slidable within the barrel and wherein the plunger sliding movement within the barrel is controlled by a power driven unit, further wherein the device comprises a motor arrangement for oscillating the barrel,
  wherein said motor arrangement is configured for, in a first premixing step, oscillating the receptacle about said longitudinal axis clockwise and counter-clockwise from a first reference point through a first angle of rotation for a first period of time and at a first angular velocity; and
  wherein said motor arrangement is configured for, in a second premixing step, oscillating the receptacle about said longitudinal axis clockwise and counter-clockwise from a second reference point through a second angle of rotation for a second period of time and at a second angular velocity; and wherein said first angle of rotation is smaller than said second angle of rotation, and said first period of time is shorter than said second period of time.

According to preferred embodiments, the method and the pump device can have one or more of the following features:

the second angle of rotation is at least three times said first angle of rotation;

the first angle of rotation (δ in FIGS. 2.2 and 3.2) is between 20° and 60°;

the second angle of rotation (γ in FIGS. 2.3 and 3.3) is between 90° and 160°;

the first period of time is 1-3 seconds and said second period of time is 10-15 seconds;

the first angular velocity is equal to said second angular velocity;

the first angular velocity and the second angular velocity are comprised between 800°/s and 2200°/s;

it is provided a combined injection/infusion and mixing step in which said liquid composition is injected while a mixing phase is carried out, wherein the receptacle is oscillated about said longitudinal axis through a third angle of rotation from a third reference point and at a third angular velocity, the combined injection/infusion and mixing step being carried out after said second premixing step. According to an embodiment of the invention, the third reference point is different from the first reference point and the second reference point; alternatively, the third reference point coincides with the first reference point and/or the second reference point. Preferably the mixing phase is continuously carried out for the whole duration of the injection/infusion phase;

the combined injection/infusion and mixing step is carried out immediately after said second premixing step;

the combined injection/infusion and mixing step is performed so that the injection/infusion phase is started simultaneously to the mixing phase; alternatively, the injection/infusion phase of the combined injection/infusion and mixing step is delayed with respect to the mixing phase. It is important that the overall mixing function (first and second premixing steps, and mixing phase of the combined injection/infusion and mixing step) is uninterrupted and not stopped;

the first premixing step comprises a step of reversing the receptacle by rotating the latter about the longitudinal axis of about 180°;

the steps of inverting the receptacle rotation comprise a pause step before each inversion of the receptacle rotation direction;

the pause step comprises stopping the receptacle rotation for a period of time of about 0.1 s; and the receptacle comprises a syringe and the liquid composition comprises an ultrasound contrast agent.

Advantageously, the premixing phase of the present invention is shorter in time with respect to the prior art initial mixing phase which occurs before the injection/infusion phase is started, e.g. the initial mixing phase that is carried out according to the teachings of EP 1 035 882 mentioned above.

According to the present invention the terms microparticles, microbubbles, microballoons or microspheres are interchangeable.

The particles of the liquid composition used in the present invention may be of various kinds and involve, for instance, microspheres containing entrapped air or other gases used in echography. These microspheres may be bounded by a liquid/gas interface (microbubbles), or they may have a tangible membrane envelope, e.g. made from synthetic polylactides or natural polymer like denatured protein such as albumin (microballoons). The carrier liquid for the microbubbles suspensions comprises surfactants, preferably saturated phospholipids in laminar or lamellar form such as diacylphosphatidyl derivatives in which the acyl group is a C16 or higher fatty acid residue.

The gases used in the microbubbles or microballoons are pure gases or gas mixtures including at least one physiologically acceptable halogenated gas. This halogenated gas is preferably selected among CF4, C2F6, C3F8, C4F8 C4F10, C5F12, C6F14 or SF6. The gas mixtures can also contain gases such as air, oxygen, nitrogen, helium, xenon or carbon dioxide. In fact in a number of cases microbubbles or microballoons will contain mixtures of nitrogen or air with at least one perfluorinated gas in proportions which may vary between 1 and 99%.

In the microballoons the membrane is made from a biodegradable material such as biodegradable polymers, solid triglycerides or proteins and are preferably selected from the polymers of polylactic or polyglycolic acid and their copolymers, denatured serum albumin, denatured hemoglobin, lower alkyl polycyanoacrylates, and esters of polyglutamic and polyaspartic acid, tripalmitin or tristearin, etc. In an embodiment, the microballoons are filled with C3Fg and the material envelope is made of albumin.

BRIEF DESCRIPTION OF DRAWINGS

The present invention will become fully clear from the following detailed description, given by way of example and not of limitation, to be read with reference to the following figures wherein:

FIGS. 2.1, 2.2 and 2.3 show, in a diagrammatic manner, a premixing step according to the example of FIG. 2;

FIGS. 3.1, 3.2 and 3.3 show, in a diagrammatic manner, a premixing step according to the example of FIG. 3;

with a solution of the prior art according to which a nominal infusion/injection phase is shown during which a mixing phase is carried out for the whole duration of the nominal infusion/injection phase.

DETAILED DESCRIPTION

Figure 1:
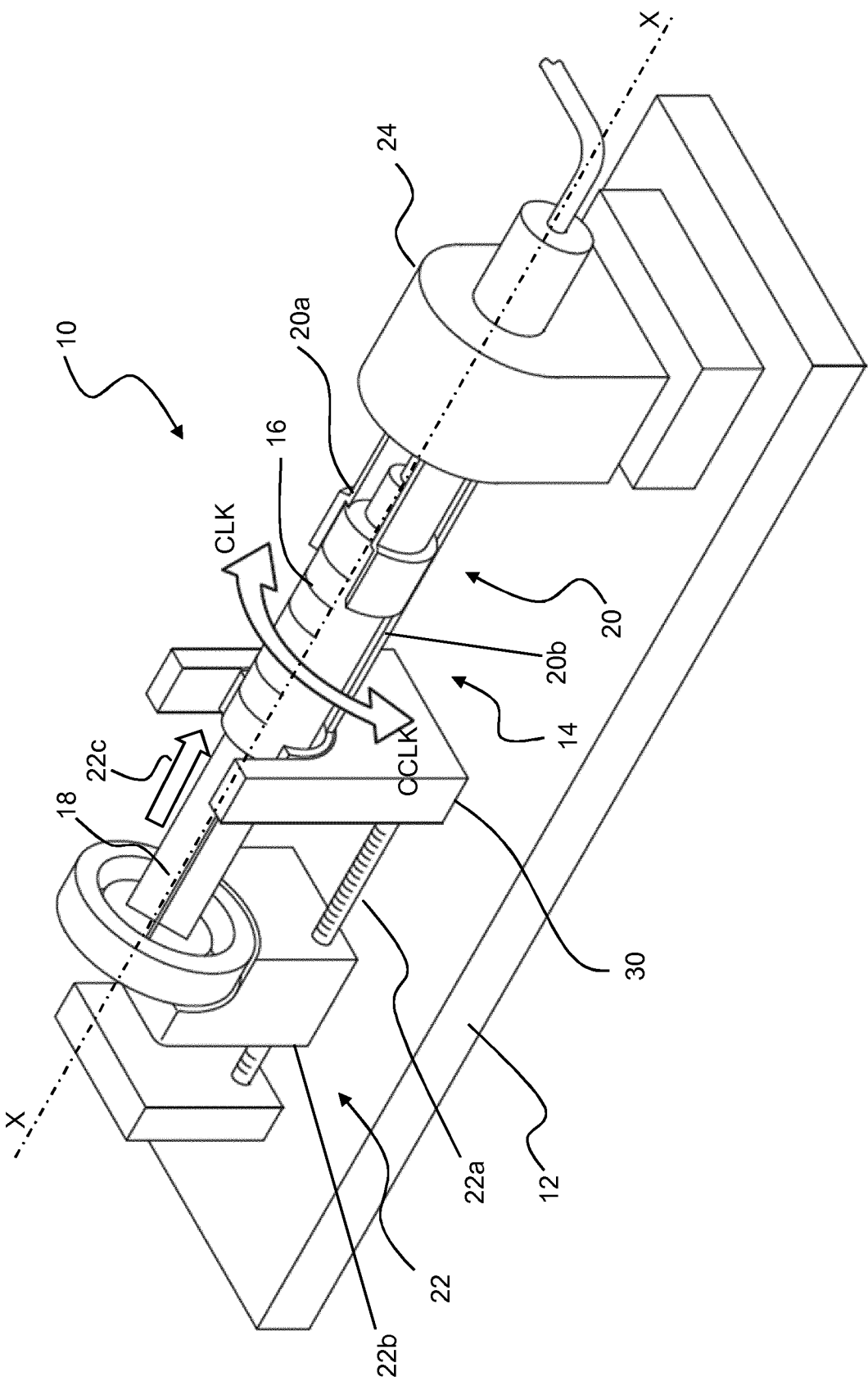
FIG. 1 shows an infusion pump device used for performing the method of the present invention.

In order to suitably investigate the premixing step parameters according to the present invention, the infusion pump device shown in FIG. 1 has been used for carrying out several tests.

In detail, the infusion pump device 10 shown in FIG. 1 comprises a base plate 12 and a syringe 14 having a barrel 16 and a plunger 18. Preferably, a longitudinal axis X-X of the syringe 14 is substantially horizontal. Preferably, the barrel 16 is supported in a rotatable fashion by a cradle arrangement 20. Preferably, the plunger 18 is sliding within the barrel 16 and the plunger displacement therein is controlled by a power driven unit 22 capable of moving forward and backward in engagement with the back pusher end of the plunger 18.

The power driven unit 22 comprises a motor means (not shown), an endless screw 22*a* and a pushing block 22*b*. The motor means rotates the endless screw 22*a*, which in turns translates the pushing block 22*b* during the injection or infusion phase. In this way, the plunger 18 (whose end provided with a flange is engaged by the pushing block 22*b*) is moved within the syringe barrel 16, and the liquid composition contained therein is pushed out and injected/infused into a patient. The movement of the plunger 18 during the injection/infusion phase is indicated by arrow 22*c*. When the injection/infusion phase is terminated, the endless screw is moved back to the starting position.

The cradle arrangement 20 comprises a first support 20*a* and a second support 20*b*, which contribute in supporting the syringe barrel in a proper aligned position between a supporting bracket 30 and a motor driven unit 24. In detail, the second support 20*b* is longitudinally extended and longitudinally supports the syringe barrel 16 for most part of its longitudinal extension. The first support 20*a* is positioned at the axial end of the syringe barrel (i.e. at the syringe nozzle exit) and it surrounds most part of the barrel cylindrical outer surface to engage and block the syringe barrel during its rotational movement.

More specifically, the cradle 20 is rotated (i.e. oscillated) about the longitudinal axis X-X of the syringe 14. The rotation can comprise an initial rotation from a rest position (starting point A of FIGS. 2.1 and 3.1) to a first reference position (first reference point B of FIGS. 2.1, 2.2 and 3.1, 3.2). Said initial rotation of about 180° is performed for making a reversal of the syringe cradle in order to start detachment of the liquid suspension microbubbles from the syringe wall. Then the rotation further comprises at least one oscillating movement from (about) said first reference position.

Figure 2:
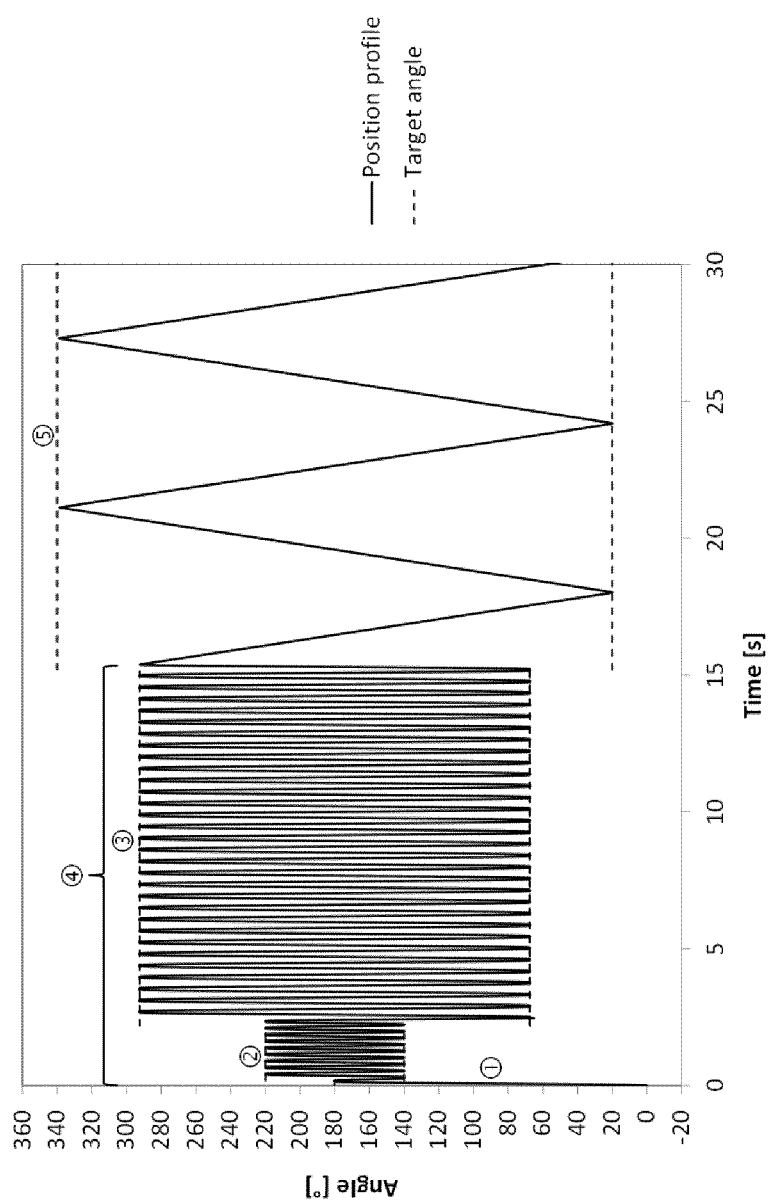
FIG. 2 shows a graph of a premixing step according to an example of the method of the present invention (wherein the second reference point coincides with the first reference point), followed by an infusion/injection and mixing step which is only partially represented (wherein the third reference point coincides with both the first reference point and the second reference point)

The term "oscillating movement" in the present description and claims is intended to mean a repetitive movement clockwise-counter-clockwise about a reference position. One example comprises:

i. a clockwise (or counter-clockwise) movement from a reference point to a first maximum rotation point at +δ degrees (e.g. point B' of FIG. 2.2) from the reference point (e.g. point B of FIG. 2.2);

ii. a counter-clockwise (or clockwise) movement from the first maximum rotation point (e.g. point B' of FIG. 2.2) to a second maximum rotation point at −δ degrees (e.g. point B" of FIG. 2.2) from the reference point (e.g. point B of FIG. 2.2);

iii. a clockwise (or counter-clockwise) movement from the second maximum rotation point to a first maximum rotation point at +δ degrees from the reference point.

Typically, an oscillating movement comprises a number of oscillations according to ii. and iii., and it is identified by an angle of rotation about the reference point. For instance, the term "±40°" indicates an oscillating rotational movement of 40° about the reference point. This means that, at regime, there is provided a clockwise-counterclockwise rotation having an overall angular extension of 80°.

Preferably, the clockwise and counterclockwise rotations are carried out at the same angular velocity.

The rotation movement can be continuous, i.e. without any pause before the rotation in an opposite direction is started. Alternatively, a pause is provided before the rotation in an opposite direction is started. In FIG. 1 the clockwise movement is indicated by arrow CLK; similarly, the counter-clockwise movement is indicated by arrow CCLK.

Preferably, the pump device 10 further comprises a control device for processing signals from a laser detector designed to read an identifying mark on the syringe. This mark is designed for preventing errors in the selection of the syringe. The code of the mark can be according to standard bar codes or color codes.

At its axial end the syringe barrel has a tip or nozzle for connecting to a liquid dispensing tubing for properly administering the liquid composition. The administration of liquid composition can be to a patient.

While the infusion pump device is, in one embodiment, configured for delivering any Ultrasound Contrast Agents (USCA) in a continuous injection/infusion mode and/or as a bolus, SonoVue™ has been used throughout the following tests.

In detail, tests have been carried out to optimize the profile of the premixing phase as well as the frequency of the mixing phase that is performed during the injection/infusion phase. Thereafter the tests verified the complete sequential profile of the premixing phase followed by the mixing phase and they demonstrated a very good re-homogenization of SonoVue™ suspension during the premixing phase as well as very satisfying and stable SonoVue™ preservation profiles in terms of microbubbles concentration and size distribution during the whole injection/infusion phase.

In order to improve the mixing of a decanted suspension, the method of injection/infusion according to the present invention comprises a premixing phase which is split into two sequential premixing steps:

a first premixing step, aimed at detaching the microbubbles (or microparticles) of the liquid suspension from the syringe barrel wall, and a second premixing step, aimed at reaching a uniform distribution of the microbubbles (or microparticles) before starting the infusion/injection phase, these microbubbles having been unstuck from the syringe barrel wall during the syringe reversal step and the first premixing step.

According to an embodiment of the present invention, the first premixing step comprises an oscillating movement (i.e. a sequence of successive clockwise and counter-clockwise rotations) about a first reference point followed by the second premixing step that is an oscillating movement about a second reference point, wherein the second reference point coincides with the first reference point (see FIG. 2). According to the invention, the overall amplitude of the oscillating movement (i.e. the overall angular extension) from (about) said second reference point is greater than the overall amplitude of the oscillating movement from said first reference point.

This embodiment is schematically shown in FIGS. 2.1, 2.2 and 2.3.

In detail, FIG. 2.1 shows a cradle (exemplified by circle 16) which is rotated of 180° to move from starting point A to first reference point B. This reversal step corresponds to step 1 of FIG. 2.

FIG. 2.2 represents the first premixing step according to which cradle 16 is oscillated from first reference point B. In particular, the diagrams of FIG. 2.2 show the sequence of successive clockwise and counter-clockwise rotations about reference point B of an angle ±δ (first angle of rotation). In more detail, in the example a clockwise rotation of +δ from reference point B to point B' is followed by a counter-clockwise rotation from point B' to point B". Successively a clockwise rotation from point B" to point B' is performed. This alternation of opposite rotations is done more times within the set first period of time of the first premixing step, which corresponds to step 2 of FIG. 2.

FIG. 2.3 represents the second premixing step according to which cradle 16 is oscillated from second reference point C that, in this example, corresponds to (coincides with) first reference point B. In particular, the diagrams of FIG. 2.3 show the sequence of successive clockwise and counter-clockwise rotations about reference point B=C of an angle ±γ (second angle of rotation). In more detail, in the shown example a clockwise rotation of +γ from reference point B=C to point C' is followed by a counter-clockwise rotation from point C' to point C". Successively a clockwise rotation from point C" to point C' is performed. This alternation of opposite rotations is done more times within the set second period of time of the second premixing step, which corresponds to step 3 of FIG. 2.

Figure 3:
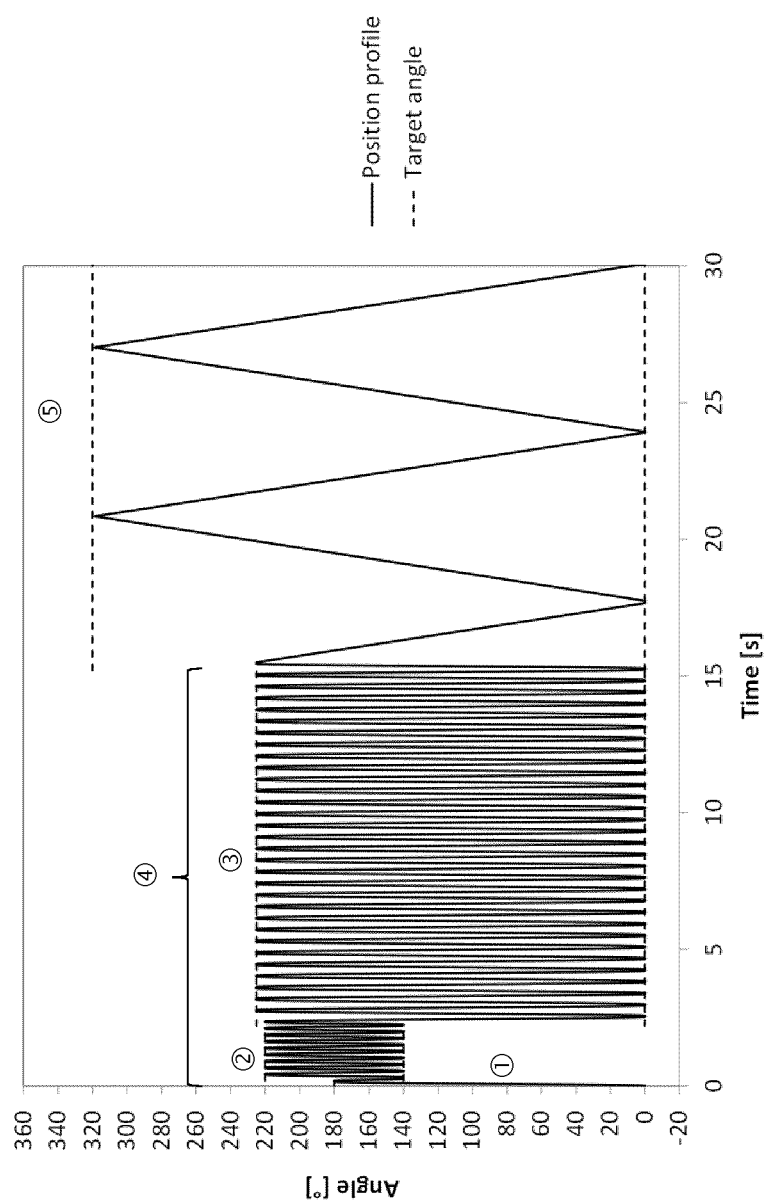
FIG. 3 shows a graph of a premixing step according to a further example of the method of the present invention (wherein the second reference point is different from the first reference point), followed by an infusion/injection and mixing step which is only partially represented (wherein the third reference point is different from the first reference point and the second reference point)

According to an alternative embodiment of the present invention, the first premixing step comprises an oscillating movement about a first reference point followed by the second premixing step that is an oscillating movement about a second reference point, wherein the second reference point is different from the first reference point (see FIG. 3). According to the invention, the overall amplitude of the oscillating movement (i.e. the overall angular extension) from (about) said second reference point is greater than the overall amplitude of the oscillating movement from said first reference point.

This embodiment is schematically shown in FIGS. 3.1, 3.2 and 3.3.

In detail, FIG. 3.1 shows a cradle (exemplified by circle 16) which is rotated of 180° to move from starting point A to first reference point B. This reversal step corresponds to step 1 of FIG. 3.

FIG. 3.2 represents the first premixing step according to which cradle 16 is oscillated from first reference point B. In particular, the diagrams of FIG. 3.2 show the sequence of successive clockwise and counter-clockwise rotations about reference point B of an angle ±δ (first angle of rotation). In more detail, in the example a clockwise rotation of +δ from reference point B to point B' is followed by a counter-clockwise rotation from point B' to point B" (and thus the overall angle of rotation is equal to 2δ). Successively a clockwise rotation from point B" to point B' is performed. This alternation of opposite rotations is done more times within the set first period of time of the first premixing step, which corresponds to step 2 of FIG. 3.

FIG. 3.3 represents the second premixing step according to which cradle 16 is oscillated from second reference point D, which is different from first reference point B of the first premixing step. In particular, the diagrams of FIG. 3.3 show a first counter-clockwise rotation from point B' (where, according to this example, the cradle is positioned at the end of the first premixing step) to starting point A. Then a sequence of successive clockwise and counter-clockwise rotations about reference point D of an angle ±γ (second angle of rotation) is started. In more detail, in the shown example a clockwise rotation from reference point A to point D' (the overall angle of rotation being equal to 2γ) is followed by a counter-clockwise rotation from point D' to point D" (which in this example coincides with starting point A). Successively a clockwise rotation from point D" to point D' is performed. This alternation of opposite rotations is done more times within the set second period of time of the second premixing step, which corresponds to step 3 of FIG. 3.

In the first and second premixing steps, variations of the angle of rotation, angular velocity and time duration were fully investigated.

In the present description, the following expressions have been used:

"reference" or "reference sample" for indicating a sample of suspension taken from the syringe barrel before starting any test (experiment) and without being subjected to any mixing or decantation; it corresponds to the nominal (real) concentration and distribution of the microbubbles;

"total microbubbles conc." (conc.=concentration) for indicating the percentage of the total microbubbles concentration of a given sample of suspension as compared to the value of the total microbubbles concentration in the reference;

"2-8 μm" or "2-8 μm microbubbles concentration" for indicating the percentage of the microbubbles having a diameter between 2 μm and 8 μm per ml of a given sample of suspension as compared to the same microbubbles diameter range concentration in the reference;

"MVC" or "microbubbles volume concentration" for indicating the percentage of total microbubbles volume (in microliter) per ml (milliliter) of a given sample of suspension as compared to the total microbubbles volume (in microliter) per ml (milliliter) in the reference.

In the present description and claims, unless otherwise specified, times are expressed in seconds (also indicated with "s" or "sec"). Angle measurements are expressed in degrees (also indicated with "deg" or "°"). Angular velocities are expressed in degrees/seconds (also indicated with "°/s").

1. Variation of the Relevant Parameters in the First Premixing Step 1.1 Preliminary Experiment For all the tests, time zero was measured with the cradle stopped for 30 minutes and before the infusion phase was started (with no mixing phase being performed during the infusion phase). Time zero samples represented the worst case of decantation, and were collected and analyzed by comparison with the reference samples.

syringe cradle was oscillated of 225° (overall amplitude of the second rotation, i.e. corresponding to 2γ) at an angular velocity of about 820°/s (this step being the second premixing step and corresponding e.g. to FIG. 3.3). This second premixing step was carried out according to the embodiment shown in FIGS. 3.1, 3.2 and 3.3, i.e. the second reference point was different from the first reference point. Between each inversion of the rotational movement (from clockwise to counter-clockwise, or vice versa), the cradle was maintained stopped for about 0.1 s (i.e. a first pause of about 0.1 s was set in the upper side of the cycle corresponding to 225°, indicated as "h" in the table, and a second pause of about 0.1 s was set in the lower side of the cycle corresponding to 0°, indicated as "b" in the table). Maintaining the cradle stopped (for a given pause time) between each cradle inversion is optional and it has not to be considered as a preferred embodiment.

TABLE 1.1

δ = ±30° at 820°/s during 5 s → 2γ = 225° at 820°/s (0.1 s(h)-0.1 s(b))

| | total microbubbles conc. | | | 2-8 μm | | | MVC | | |
| --- | --- | --- | --- | --- | --- | --- | --- | --- | --- |
| | | | | time in (s) | | | | | |
| | 0 | 22 | 37 | 0 | 22 | 37 | 0 | 22 | 37 |
| Vial #1 Ratio | 33.6% | 86.5% | 93.2% | 9.8% | 86.2% | 89.0% | 2.7% | 92.2% | 83.8% |
| Vial #2 Ratio | 35.0% | 86.3% | 94.4% | 9.0% | 86.7% | 99.7% | 2.8% | 86.1% | 111.4% |
| Vial #3 Ratio | 34.1% | 86.7% | 100.9% | 11.1% | 84.9% | 102.2% | 2.6% | 84.0% | 103.2% |
| Average | 34.3% | 86.5% | 96.2% | 10.0% | 85.9% | 96.9% | 2.7% | 87.4% | 99.4% |
| std. dev. | 0.7% | 0.2% | 4.2% | 1.0% | 0.9% | 7.0% | 0.1% | 4.3% | 14.2% |

1.2 Angular Velocity of the Rotation During the First Premixing Step

A series of tests was carried out to establish the appropriate angular velocity of the infusion pump device for the first premixing step.

Tests were carried out at an angular velocity of 820°/s and at an angular velocity of 2000°/s, respectively.

The obtained results were compared between these two angular velocities for a first premixing step time duration of 5 seconds, while not varying the parameters of the second premixing step.

The experimentation was repeated three times (vials 1 to 3 in the tables). The results were calculated as % with respect to the reference samples, and averages were presented in percent.

The following Tables 1.1 and 1.2 present the evolution of the liquid suspension characteristics (focused on total microbubbles concentration, 2-8 μm microbubbles concentration and microbubbles volume concentration (MVC)).

The first test of this series was carried out by oscillating (rotating) the syringe cradle between ±30° (first angle of rotation δ) at an angular velocity of about 820°/s for a period of time of 5 s (this step being the first premixing step and corresponding e.g. to FIG. 3.2), followed by a step where the The second test of this series was carried out by oscillating (rotating) the syringe cradle between ±30° (first angle of rotation δ) at an angular velocity of about 2000°/s for a period of time of 5 s (this step being the first premixing step and corresponding e.g. to FIG. 3.2), followed by a step where the syringe cradle was oscillated (rotated) of 225° (overall amplitude of second rotation, i.e. corresponding to 2γ) at an angular velocity of about 820°/s (this step being the second premixing step and corresponding e.g. to FIG. 3.3). This second premixing step was carried out according to the embodiment shown in FIGS. 3.1, 3.2 and 3.3, i.e. the second reference point was different from the first reference point. Between each inversion of the rotational movement the cradle was maintained stopped for about 0.1 s (i.e. a first pause was set in the upper side of the cycle corresponding to 225°, indicated as "h" in the table, and a second pause was set in the lower side of the cycle corresponding to 0°, indicated as "b" in the table). Maintaining the cradle stopped (for a given pause time) between each cradle inversion is optional and it has not to be considered as a preferred embodiment.

TABLE 1.2

| | δ = ±30° at 2000°/s during 5 s → 2γ = 225° at 820°/s (0.1 s(h)-0.1 s(b)) | | | | | | | | |
|---|---|---|---|---|---|---|---|---|---|
| | total microbubbles conc | | | 2-8 µm | | | MVC | | |
| | | | | time in (s) | | | | | |
| | 0 | 17 | 22 | 0 | 17 | 22 | 0 | 17 | 22 |
| Vial #1 Ratio | 33.6% | 75.3% | 86.8% | 9.8% | 79.9% | 84.9% | 2.7% | 90.8% | 80.4% |
| Vial #2 Ratio | 35.0% | 81.4% | 89.8% | 9.0% | 75.1% | 87.8% | 2.8% | 76.8% | 93.3% |
| Vial #3 Ratio | 34.1% | 72.1% | 92.8% | 11.1% | 76.4% | 94.9% | 2.6% | 81.8% | 98.0% |
| Average | 34.3% | 76.2% | 89.8% | 10.0% | 77.2% | 89.2% | 2.7% | 83.2% | 90.6% |
| std. dev. | 0.7% | 4.7% | 3.0% | 1.0% | 2.5% | 5.1% | 0.1% | 7.1% | 9.1% |

This first series of tests showed that the results with angular velocity of 2000°/s were slightly better than those at angular velocity of 820°/s.

1.3 Angle of Rotation During the First Premixing Step

The following Tables 2.1 to 2.5 present the liquid suspension characteristics (focused on total microbubbles concentration, 2-8 µm microbubbles concentration and microbubbles volume concentration (MVC)) at different first angles of rotation δ during the first premixing step. The tested angles of rotation δ were ±20°, ±30°, ±40°, ±50°, ±60°. For each angle of rotation, the cradle and syringe assembly was oscillated (rotated) at 2000°/s for a duration time of 5 seconds (first premixing step) and then oscillated (rotated) of 225° (overall amplitude of the second rotation, i.e. corresponding to 2γ) at 820°/s (second premixing step). This second premixing step was carried out according to the embodiment shown in FIGS. 3.1, 3.2 and 3.3, i.e. the second reference point was different from the first reference point.

All the obtained results were compared to the reference samples and presented in percent.

The first test of this series was carried out by oscillating the syringe cradle of ±20° (first angle of rotation δ) for 5 seconds at an angular velocity of about 2000°/s (this step being the first premixing step and corresponding e.g. to phase FIG. 3.2), followed by a step where the syringe cradle was oscillated of 225° (overall amplitude of the second rotation, i.e. corresponding to 2γ) at an angular velocity of about 820°/s (this step being the second premixing step and corresponding e.g. to FIG. 3.3). Between each inversion of the rotational movement the cradle was maintained stopped for about 0.1 s (i.e. a first pause was set in the upper side of the cycle corresponding to 225°, indicated as "h" in the tables, and a second pause was set in the lower side of the cycle corresponding to 0°, indicated as "b" in the tables). Maintaining the cradle stopped (for a given pause time) between each cradle inversion is optional and it has not to be considered as a preferred embodiment.

TABLE 2.1

| | δ = ±20° at 2000°/s during 5 s → 2γ = 225° at 820°/s (0.1 s(h)-0.1 s(b)) | | | | | |
|---|---|---|---|---|---|---|
| | total microbubbles conc | | 2-8 µm | | MVC | |
| | | | time in (s) | | | |
| | 0 | 17 | 0 | 17 | 0 | 17 |
| Vial #1 Ratio | 33.6% | 81.7% | 9.8% | 77.2% | 2.7% | 71.3% |
| Vial #2 Ratio | 35.0% | 87.3% | 9.0% | 84.1% | 2.8% | 85.9% |
| Vial #3 Ratio | 34.1% | 75.9% | 11.1% | 73.0% | 2.6% | 76.8% |
| Average | 34.3% | 81.6% | 10.0% | 78.1% | 2.7% | 78.0% |
| std. dev. | 0.7% | 5.7% | 1.0% | 5.6% | 0.1% | 7.4% |

The second test of this series was carried out by oscillating the syringe cradle of ±30° (first angle of rotation δ) for the same time as the first test and at the same angular velocity. All the other conditions were maintained unchanged.

TABLE 2.2

| | δ = ±30° at 2000°/s during 5 s → 2γ = 225° at 820°/s (0.1 s(h)-0.1 s(b)) | | | | | | | | |
|---|---|---|---|---|---|---|---|---|---|
| | total microbubbles conc | | | 2-8 µm | | | MVC | | |
| | | | | time in (s) | | | | | |
| | 0 | 17 | 22 | 0 | 17 | 22 | 0 | 17 | 22 |
| Vial #1 Ratio | 33.6% | 75.3% | 86.8% | 9.8% | 79.9% | 84.9% | 2.7% | 90.8% | 80.4% |
| Vial #2 Ratio | 35.0% | 81.4% | 89.8% | 9.0% | 75.1% | 87.8% | 2.8% | 76.8% | 93.3% |
| Vial #3 Ratio | 34.1% | 72.1% | 92.8% | 11.1% | 76.4% | 94.9% | 2.6% | 81.8% | 98.0% |
| Average | 34.3% | 76.2% | 89.8% | 10.0% | 77.2% | 89.2% | 2.7% | 83.2% | 90.6% |
| std. dev. | 0.7% | 4.7% | 3.0% | 1.0% | 2.5% | 5.1% | 0.1% | 7.1% | 9.1% |

The third test of this series was carried out by oscillating the syringe cradle of ±40° (first angle of rotation δ) for the same time as the first test and at the same angular velocity. All the other conditions were maintained unchanged.

TABLE 2.3

δ = ±40° at 2000°/s during 5 s → 2γ = 225° at 820°/s (0.1 s(h)-0.1 s(b))

| | total microbubbles conc | | 2-8 μm | | MVC | |
|---|---|---|---|---|---|---|
| | | | time in (s) | | | |
| | 0 | 17 | 0 | 17 | 0 | 17 |
| Vial #1 Ratio | 33.6% | 89.3% | 9.8% | 91.5% | 2.7% | 85.0% |
| Vial #2 Ratio | 35.0% | 89.4% | 9.0% | 88.4% | 2.8% | 91.9% |
| Vial #3 Ratio | 34.1% | 81.1% | 11.1% | 74.5% | 2.6% | 75.6% |
| Average | 34.3% | 86.6% | 10.0% | 84.8% | 2.7% | 84.2% |
| std. dev. | 0.7% | 4.8% | 1.0% | 9.1% | 0.1% | 8.2% |

The fourth test of this series was carried out by oscillating the syringe cradle of ±50° (first angle of rotation δ) for the same time as the first test and at the same angular velocity. All the other conditions were maintained unchanged.

TABLE 2.4

δ = ±50° at 2000°/s during 5 s → 2γ = 225° at 820°/s (0.1 s(h)-0.1 s(b))

| | total microbubbles conc | | 2-8 μm | | MVC | |
|---|---|---|---|---|---|---|
| | | | time in (s) | | | |
| | 0 | 17 | 0 | 17 | 0 | 17 |
| Vial #1 Ratio | 33.6% | 84.4% | 9.8% | 88.4% | 2.7% | 89.6% |
| Vial #2 Ratio | 35.0% | 87.8% | 9.0% | 87.7% | 2.8% | 84.0% |
| Vial #3 Ratio | 34.1% | 84.1% | 11.1% | 81.7% | 2.6% | 79.8% |
| Average | 34.3% | 85.5% | 10.0% | 85.9% | 2.7% | 84.5% |
| std. dev. | 0.7% | 2.1% | 1.0% | 3.7% | 0.1% | 4.9% |

The fifth test of this series was carried out by oscillating the syringe cradle of ±60° (first angle of rotation δ) for the same time as the first test and at the same angular speed. All the other conditions were maintained unchanged.

TABLE 2.5

δ = ±60° at 2000°/s during 5 s → 2γ = 225° at 820°/s (0.1 s(h)-0.1 s(b))

| | total microbubbles conc | | 2-8 μm | | MVC | |
|---|---|---|---|---|---|---|
| | | | time in (s) | | | |
| | 0 | 17 | 0 | 17 | 0 | 17 |
| Vial #1 Ratio | 33.6% | 90.0% | 9.8% | 83.6% | 2.7% | 91.0% |
| Vial #2 Ratio | 35.0% | 78.3% | 9.0% | 89.9% | 2.8% | 97.8% |
| Vial #3 Ratio | 34.1% | 82.7% | 11.1% | 84.3% | 2.6% | 83.0% |
| Average | 34.3% | 83.7% | 10.0% | 86.0% | 2.7% | 90.6% |
| std. dev. | 0.7% | 5.9% | 1.0% | 3.4% | 0.1% | 7.4% |

It can be seen from the data in the tables that the best conditions were obtained with an angle of rotation from 40° to 60°. Angles of rotation lower than 40° provided less satisfactory results, especially in terms of total microbubbles concentration and percentage of microbubbles having a size between 2 μm and 8 μm.

1.4 Time Duration of the First Premixing Step

The Applicant has further investigated the first premixing step in order to establish which is the best time duration of the first premixing step.

Tables 3.1 to 3.3 present the test results focused on total microbubbles concentration, 2-8 μm microbubbles concentration and microbubbles volume concentration (MVC)) at different time durations. The aim of the tests were to have a first premixing step with a time duration as short as possible, followed by a second premixing step that was performed at operational parameters different from those of the first premixing step.

Figure 4A:
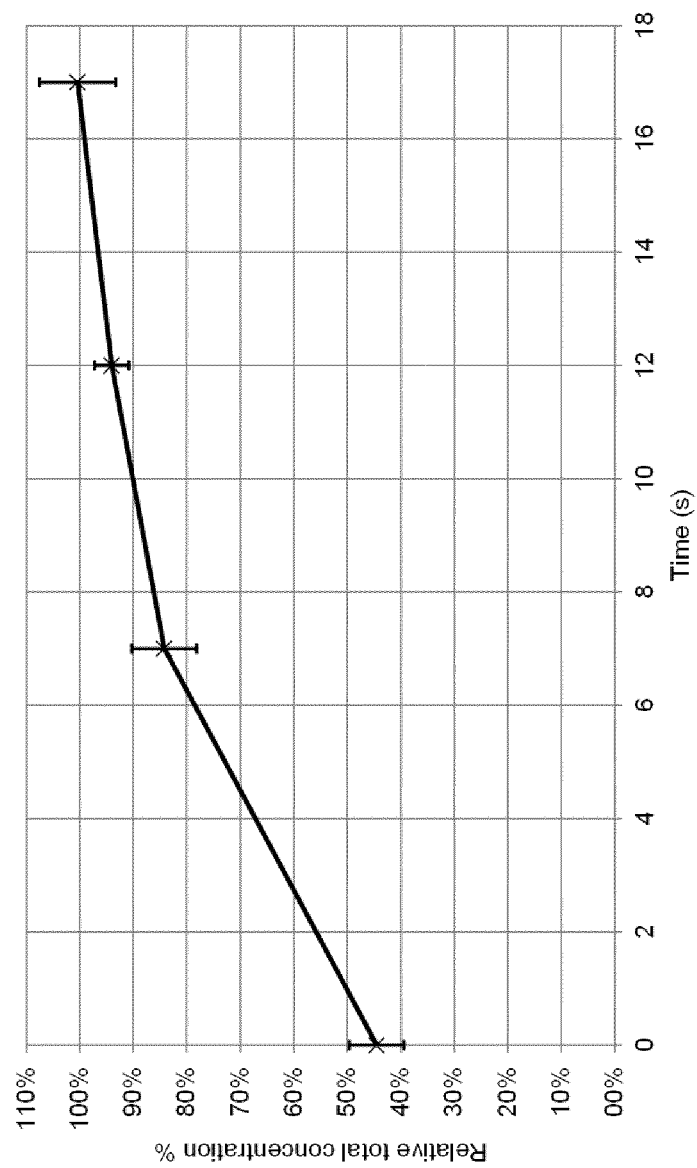
FIGS. 4a, 4b and 4c are graphs presenting the liquid suspension characteristics during the premixing step according to a preferred configuration of the present invention.
Figure 4B:
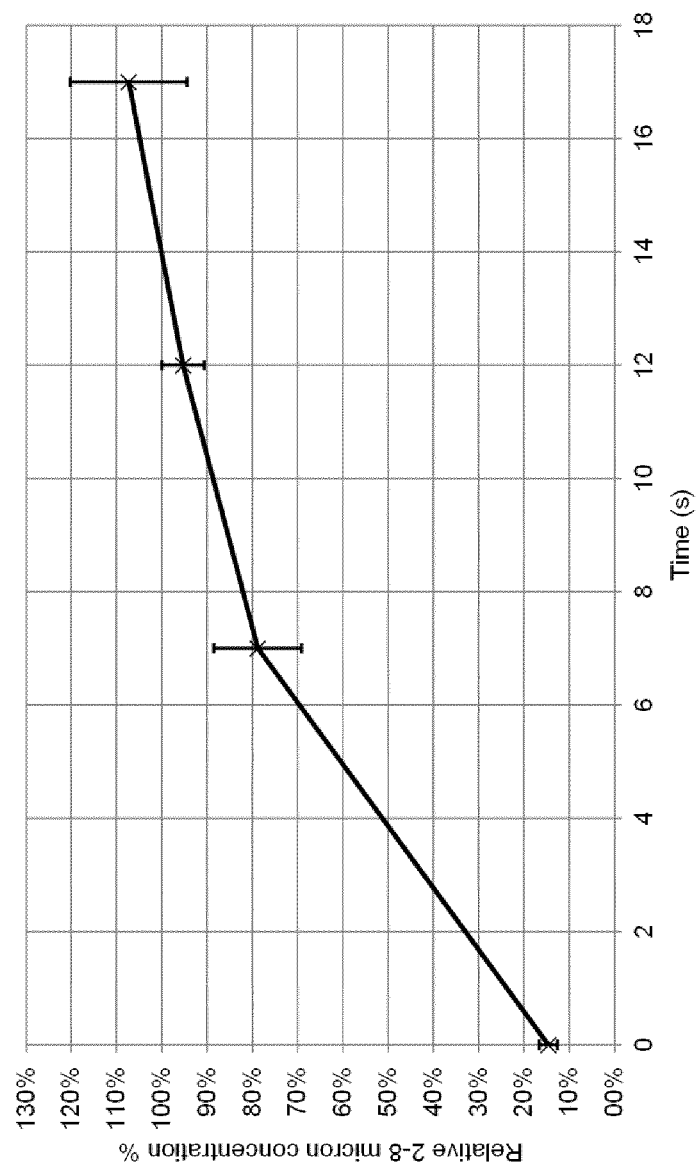
Figure 4C:
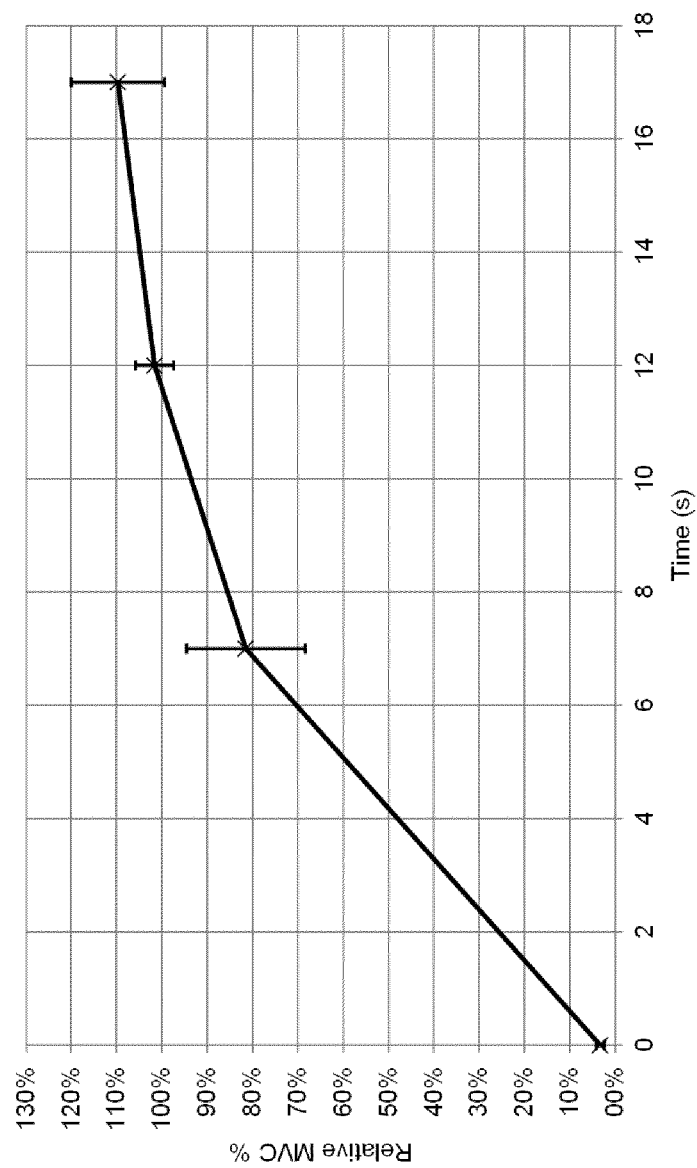

All the obtained results were compared to the reference samples and presented in percent. Each point of the curves represented in FIGS. 4a-4c is an average of at least three measures. These curves are obtained from the data listed in Table 3.3.

The study showed that 2 seconds for the first premixing step were enough effective to unstick the microbubbles from the syringe barrel wall and then to obtain a well-mixed suspension within the syringe. Furthermore, a first angle of rotation of 40° was shown to be more effective compared with a first angle of rotation of 60°.

More in detail, in a first test (see Table 3.1), the following conditions were tested: first angle of rotation δ of ±60°, angular velocity of 2000°/s, time duration of the first premixing step of 3 sec. This first premixing step was followed by a second premixing step with an overall amplitude of the second rotation of 225° (=2γ) and an angular velocity of 2000°/s. Between each inversion of the rotational movement the cradle was maintained stopped for about 0.1 s (i.e. a first pause was set in the upper side of the cycle corresponding to 225°, indicated as "h" in the tables, and a second pause was set in the lower side of the cycle corresponding to 0°, indicated as "b" in the tables). Maintaining the cradle stopped (for a given pause time) between each cradle inversion is optional and it has not to be considered as a preferred embodiment.

TABLE 3.1

| | δ = ±60° at 2000°/s during 3 s → 2γ = 225° at 2000°/s (0.1 s(h)-0.1 s(b)) | | | | | | | | | | | |
|---|---|---|---|---|---|---|---|---|---|---|---|---|
| | Total microbubbles conc | | | | 2-8 μm time in (s) | | | | MVC | | | |
| | 0 | 7 | 12 | 17 | 0 | 7 | 12 | 17 | 0 | 7 | 12 | 17 |
| Vial #1 Ratio | 48.10% | 87.2% | 89.9% | 101.1% | 16.53% | 86.4% | 89.1% | 103.3% | 4.48% | 84.0% | 91.2% | 114.3% |
| Vial #2 Ratio | 37.91% | 83.4% | 78.8% | 105.7% | 11.98% | 76.7% | 80.3% | 114.0% | 2.43% | 84.4% | 83.1% | 124.5% |
| Vial #3 Ratio | 48.90% | 78.7% | 90.4% | 104.1% | 13.90% | 73.7% | 94.5% | 116.1% | 3.08% | 76.7% | 98.9% | 129.2% |
| Vial #4 Ratio | 42.96% | 87.9% | 83.9% | 96.0% | 15.80% | 80.9% | 81.8% | 83.3% | 3.27% | 92.6% | 81.8% | 89.1% |
| Vial #5 Ratio | | 82.5% | 99.6% | 106.5% | | 74.3% | 98.7% | 119.4% | | 72.5% | 99.5% | 117.3% |
| Vial #6 Ratio | | 81.8% | 120.5% | 101.3% | | 76.9% | 119.4% | 100.0% | | 74.9% | 129.0% | 100.6% |
| Vial #7 Ratio | | 81.9% | | | | 74.9% | | | | 75.3% | | |
| Average | 44.5% | 83.4% | 93.9% | 102.5% | 14.6% | 77.7% | 94.0% | 106.0% | 3.3% | 80.1% | 97.3% | 112.5% |
| std. dev. | 5.1% | 3.2% | 14.8% | 3.9% | 2.0% | 4.5% | 14.3% | 13.4% | 0.9% | 7.2% | 17.3% | 15.1% |

In a second test (see Table 3.2), the following conditions were tested: first angle of rotation δ of ±60°, angular velocity of 2000°/s, time duration of the first premixing step of 2 sec. This first premixing step was followed by a second premixing step with an overall amplitude of the second rotation of 225° (=2γ) and an angular velocity of 2000°/s.

TABLE 3.2

| | δ = ±60° at 2000°/s during 2 s → 2γ = 225° at 2000°/s (0.1 s(h)-0.1 s(b)) | | | | | | | | | | | |
|---|---|---|---|---|---|---|---|---|---|---|---|---|
| | Total microbubbles conc | | | | 2-8 μm time in (s) | | | | MVC | | | |
| | 0 | 7 | 12 | 17 | 0 | 7 | 12 | 17 | 0 | 7 | 12 | 17 |
| Vial #1 Ratio | 48.10% | 87.2% | 84.6% | 93.3% | 16.53% | 74.7% | 80.9% | 96.2% | 4.48% | 79.4% | 87.6% | 99.2% |
| Vial #2 Ratio | 37.91% | 80.0% | 96.7% | 103.7% | 11.98% | 74.9% | 97.5% | 116.4% | 2.43% | 75.4% | 105.1% | 126.3% |
| Vial #3 Ratio | 48.90% | 75.4% | 85.2% | 92.1% | 13.90% | 81.2% | 91.1% | 107.9% | 3.08% | 81.2% | 99.8% | 118.0% |
| Vial #4 Ratio | 42.96% | | | | 15.80% | | | | 3.27% | | | |
| Average | 44.5% | 80.9% | 88.9% | 96.4% | 14.6% | 77.0% | 89.8% | 106.8% | 3.3% | 78.6% | 97.5% | 114.5% |
| std. dev. | 5.1% | 6.0% | 6.8% | 6.4% | 2.0% | 3.7% | 8.3% | 10.1% | 0.9% | 3.0% | 9.0% | 13.9% |

In a third test (see Table 3.3), the following conditions were tested: first angle of rotation δ of ±40°, angular velocity of 2000°/s, time duration of the first premixing step of 2 sec. This first premixing step was followed by a second premixing step with an overall amplitude of the second rotation of 225° (=2γ) and an angular velocity of 2000°/s. These values are the ones exemplified in FIG. 3.

TABLE 3.3

| | δ = ±40° at 2000°/s during 2 s → 2γ = 225° at 2000°/s (0.1 s(h)-0.1 s(b)) | | | | | | | | | | | |
|---|---|---|---|---|---|---|---|---|---|---|---|---|
| | Total microbubbles conc | | | | 2-8 μm time in (s) | | | | MVC | | | |
| | 0 | 7 | 12 | 17 | 0 | 7 | 12 | 17 | 0 | 7 | 12 | 17 |
| Vial #1 Ratio | 48.10% | 94.3% | 96.8% | 99.8% | 16.53% | 95.4% | 98.2% | 106.7% | 4.48% | 102.5% | 105.7% | 102.9% |
| Vial #2 Ratio | 37.91% | 86.9% | 91.3% | 106.0% | 11.98% | 81.9% | 94.0% | 115.9% | 2.43% | 91.3% | 105.3% | 119.2% |
| Vial #3 Ratio | 48.90% | 85.4% | 94.7% | 104.3% | 13.90% | 75.5% | 93.4% | 115.2% | 3.08% | 76.1% | 96.2% | 116.1% |
| Vial #4 Ratio | 42.96% | 76.9% | 92.59% | 94.4% | 15.80% | 66.0% | 100.2% | 98.6% | 3.27% | 65.9% | 99.4% | 103.8% |
| Vial #5 Ratio | | 82.0% | 98.45% | 108.0% | | 78.8% | 98.5% | 120.9% | | 77.1% | 105.1% | 120.6% |
| Vial #6 Ratio | | 79.7% | 90.31% | 89.7% | | 75.0% | 87.3% | 86.6% | | 76.2% | 98.2% | 95.5% |
| Average | 44.5% | 84.2% | 94.0% | 100.4% | 14.6% | 78.8% | 95.3% | 107.3% | 3.3% | 81.5% | 101.6% | 109.7% |
| std. dev. | 5.1% | 6.1% | 3.2% | 7.1% | 2.0% | 9.7% | 4.7% | 12.9% | 0.9% | 13.1% | 4.2% | 10.3% |

From the above, it follows that the best conditions for the first premixing step were a first angle of rotation of 40°, an angular velocity of 2000°/s and a duration time of 2 sec.

2. Variation of the Parameters in the Second Premixing Step

After the first premixing step, the microbubbles resulted to be unstuck from the syringe barrel wall, but the Applicant performed further tests to establish the best conditions for the second premixing step which is aimed at obtaining a uniform distribution of the microbubbles (which have been unstuck from the syringe barrel wall during the first premixing step).

2.1 Angle of Rotation During the Second Premixing Step

Tables 4.1 to 4.3 show the values of the liquid suspension characteristics (focused on total microbubbles concentration, 2-8 μm microbubbles concentration and microbubbles volume concentration (MVC)) for different second angles of rotation during the second premixing step.

For this test, the first premixing step was set to zero, i.e. no first premixing step was performed (i.e. no phase 2 in FIGS. 2 and 3). In all the tests, the angular velocity was set to 2000°/s.

As shown in the tables reported below the best conditions (i.e. reaching as fast as possible the 100% total microbubbles concentration) were obtained with an overall amplitude of the second rotation of 225° (=2γ). As in the previous tests described above, between each inversion of the rotational movement the cradle was maintained stopped for about 0.1 s (i.e. a first pause was set in the upper side of the cycle corresponding to 225°, indicated as "h" in the tables, and a second pause was set in the lower side of the cycle corresponding to 0°, indicated as "b" in the tables). Maintaining the cradle stopped (for a given pause time) between each cradle inversion is optional and it has not to be considered as a preferred embodiment.

TABLE 4.1

2γ = 225° at 2000°/s - 0.1 s(h)-0.1 s(b)

| | Total microbubbles conc | | | | 2-8 μm time in (s) | | | | MVC | | | |
|---|---|---|---|---|---|---|---|---|---|---|---|---|
| | 0 | 7 | 12 | 17 | 0 | 7 | 12 | 17 | 0 | 7 | 12 | 17 |
| Vial #1 Ratio | 48.10% | 82.5% | 93.6% | 108.3% | 16.53% | 75.8% | 92.6% | 114.7% | 4.48% | 77.7% | 98.2% | 120.5% |
| Vial #2 Ratio | 37.91% | 87.2% | 109.0% | 96.1% | 11.98% | 82.7% | 96.4% | 102.6% | 2.43% | 80.4% | 91.6% | 110.3% |
| Vial #3 Ratio | 48.90% | 93.5% | 85.3% | 92.3% | 13.90% | 91.0% | 87.0% | 89.8% | 3.08% | 96.5% | 84.8% | 91.5% |
| Vial #4 Ratio | 42.96% | 78.3% | 96.6% | 100.9% | 15.80% | 88.4% | 84.9% | 89.0% | 3.27% | 90.0% | 84.1% | 89.6% |
| Vial #5 Ratio | | 64.9% | 86.4% | 105.0% | | 56.8% | 92.8% | 104.7% | | 55.7% | 98.0% | 114.0% |
| Vial #6 Ratio | | 93.8% | 87.1% | 86.8% | | 84.1% | 79.7% | 93.0% | | 79.4% | 80.2% | 98.3% |
| Vial #7 Ratio | | 84.2% | | | | 73.8% | | | | 77.0% | | |
| Average | 44.5% | 83.5% | 93.0% | 98.2% | 14.6% | 78.9% | 88.9% | 99.0% | 3.3% | 79.5% | 89.5% | 104.0% |
| std. dev. | 5.1% | 10.0% | 9.0% | 8.1% | 2.0% | 11.5% | 6.2% | 10.1% | 0.9% | 12.8% | 7.6% | 12.7% |

TABLE 4.2

2γ = 320° at 2000°/s - 0.1 s(h)-0.1 s(b)

| | Total microbubbles conc | | | | 2-8 μm time in (s) | | | | MVC | | | |
|---|---|---|---|---|---|---|---|---|---|---|---|---|
| | 0 | 7 | 12 | 17 | 0 | 7 | 12 | 17 | 0 | 7 | 12 | 17 |
| Vial #1 Ratio | 48.10% | 77.6% | 91.9% | 84.3% | 16.53% | 74.0% | 89.4% | 93.8% | 4.48% | 70.6% | 87.8% | 100.6% |
| Vial #2 Ratio | 37.91% | 74.7% | 74.4% | 101.8% | 11.98% | 73.0% | 74.3% | 90.1% | 2.43% | 72.6% | 75.1% | 97.0% |
| Vial #3 Ratio | 48.90% | 82.7% | 91.8% | 93.0% | 13.90% | 70.6% | 88.4% | 92.5% | 3.08% | 73.1% | 88.9% | 97.3% |
| Vial #4 Ratio | 42.96% | | 86.6% | | 15.80% | | 81.5% | | 3.27% | | 86.5% | |
| Average | 44.5% | 78.3% | 86.2% | 93.0% | 14.6% | 72.5% | 83.4% | 92.1% | 3.3% | 72.1% | 84.6% | 98.3% |
| std. dev. | 5.1% | 4.0% | 8.2% | 8.8% | 2.0% | 1.8% | 7.0% | 1.9% | 0.9% | 1.3% | 6.4% | 2.0% |

TABLE 4.3

| | Total microbubbles conc | | | | 2-8 μm time in (s) | | | | MVC | | | |
|---|---|---|---|---|---|---|---|---|---|---|---|---|
| | 0 | 7 | 12 | 17 | 0 | 7 | 12 | 17 | 0 | 7 | 12 | 17 |
| Vial #1 Ratio | 48.10% | 81.0% | 88.2% | 88.3% | 16.53% | 73.8% | 85.5% | 87.0% | 4.48% | 71.4% | 86.6% | 86.9% |
| Vial #2 Ratio | 37.91% | 83.8% | 86.5% | 90.2% | 11.98% | 76.8% | 77.9% | 89.2% | 2.43% | 81.6% | 87.5% | 86.7% |
| Vial #3 Ratio | 48.90% | 72.9% | 100.8% | 92.9% | 13.90% | 67.4% | 100.5% | 93.2% | 3.08% | 67.3% | 109.4% | 95.4% |
| Vial #4 Ratio | 42.96% | | | | 15.80% | | | | 3.27% | | | |
| Average | 44.5% | 79.2% | 91.9% | 90.5% | 14.6% | 72.7% | 88.0% | 89.8% | 3.3% | 73.5% | 94.5% | 89.7% |
| std. dev. | 5.1% | 5.7% | 7.8% | 2.3% | 2.0% | 10.1% | 2.6% | 5.1% | 0.9% | 13.3% | 5.3% | 8.6% |

$2\gamma = 180°$ at $2000°/s$ - $0.1$ $s(h)$-$0.1$ $s(b)$

As already mentioned above, SonoVue™ suspension settles relatively rapidly if not mixed. According to prior art solutions, as previously indicated, an initial mixing phase was arranged in order to re-suspend the microbubbles of the liquid suspension before starting an infusion or an injection phase and then the same initial mixing phase was carried out also during the infusion/injection phase. The initial mixing phase (occurring before the infusion/injection phase was started) was carried out in a single step lasting at least about 90 seconds. The Applicant perceived that this time duration, before an injection/infusion phase can be effectively performed, was too long and aimed at making more efficient the mixing phase occurring before the infusion/injection phase is started in order to reduce the mixing phase time duration.

Therefore, according to the present invention, a premixing phase is performed which is split in two distinct premixing steps that are carried out according to different operational (premixing) parameters. In detail, the premixing phase comprises a first premixing step according to first operational parameters followed by a second premixing step according to second operational parameters. Even though the first and second premixing steps are not separated and are performed in sequence without any pause in between, the premixing phase according to the present invention is considered as a two-steps premixing phase.

According to the tests performed by the Applicant using SonoVue™ as a contrast agent, the first premixing step should be short in time and should be carried out by reciprocating the syringe with a first angle of rotation at a first angular velocity, while the second premixing step should be longer in time than the first premixing step and should be carried out by reciprocating the syringe with a second angle of rotation at a second angular velocity.

Therefore, according to an embodiment of the present invention, the first time duration t1 corresponding to the first premixing step is shorter than the second time duration t2 corresponding to the second premixing step. Preferably, the second time duration t2 is at least 3-4 times greater than the first time duration t1.

According to an embodiment, the first time duration t1 is about 1 to 3 seconds. Preferably, the first time duration t1 is about 2 seconds.

According to an embodiment, the second time duration t2 is about 10-20 seconds. Preferably, the second time duration t2 is about 11-16 seconds. More preferably, the second time duration t2 is about 12-15 seconds. Still more preferably, the second time duration t2 is about 12-13 seconds.

According to an embodiment, the first angle of rotation δ of the first premixing step is between about 20° and 60°.

Preferably, the first angle of rotation δ is between about 30° and 50°. More preferably, the first angle of rotation δ is equal to about 40°.

Preferably, the second angle of rotation γ of the second premixing step is higher than the first angle of rotation δ. More preferably, the second angle of rotation γ is between three and five times greater than the first angle of rotation δ.

According to an embodiment, the second angle of rotation γ is between about 90° and 160°. Preferably, the second angle of rotation γ is between about 105° and 115°. More preferably, the second angle of rotation γ is equal to about 112.5°.

Preferably, the angular velocity ω (i.e. the rotation velocity) of the syringe is higher than 1000°/s. More preferably, the angular velocity ω is about 2000°/s.

As already anticipated above, FIGS. 2 and 3 show in a diagrammatic manner the premixing phase according to the present invention as well as a first portion of the successive injection/infusion and mixing phase (i.e. the mixing step that is carried out during the whole duration of the injection step). The graph presents a typical premixing profile (cradle angle of rotation as a function of time) with the two (first and second) premixing steps followed by the injection/infusion phase which includes a mixing phase.

In detail FIGS. 2 and 3 show the following steps and phases according to an embodiment of the present invention:

Phase 1: it represents the syringe cradle reversal that is obtained by rotating the cradle of 180° (see FIGS. 2, 2.1 and 3, 3.1);

Phase 2: it represents the first premixing step for detaching the microbubbles from the syringe wall (see FIGS. 2, 2.2 and 3, 3.2);

Phase 3: it represents the second premixing step for uniformly distributing the microbubbles within the syringe barrel (see FIGS. 2, 2.3 and 3, 3.3);

Phase 4: it represents the overall sequence of cradle reversal and premixing (i.e. it is the combination of Phases 1 to 3) (see FIGS. 2 and 3);

Phase 5: it represents the mixing phase that is performed during the injection/infusion phase (see FIGS. 2 and 3).

FIGS. 4a, 4b and 4c are obtained from the data shown in Table 3.3. These graphs represent the evolution of the suspension characteristics (focused on total microbubbles concentration, 2-8 μm microbubbles concentration and microbubbles volume concentration (MVC)) of a decanted suspension (30 minutes without mixing) with a preferred configuration according to the present invention. As it can be seen, in these conditions (i.e. the operational parameters defined in FIG. 3), a suspension of SonoVue™ left at rest for 30 minutes is well re-suspended in approximately 15 seconds.

Figure 5A:
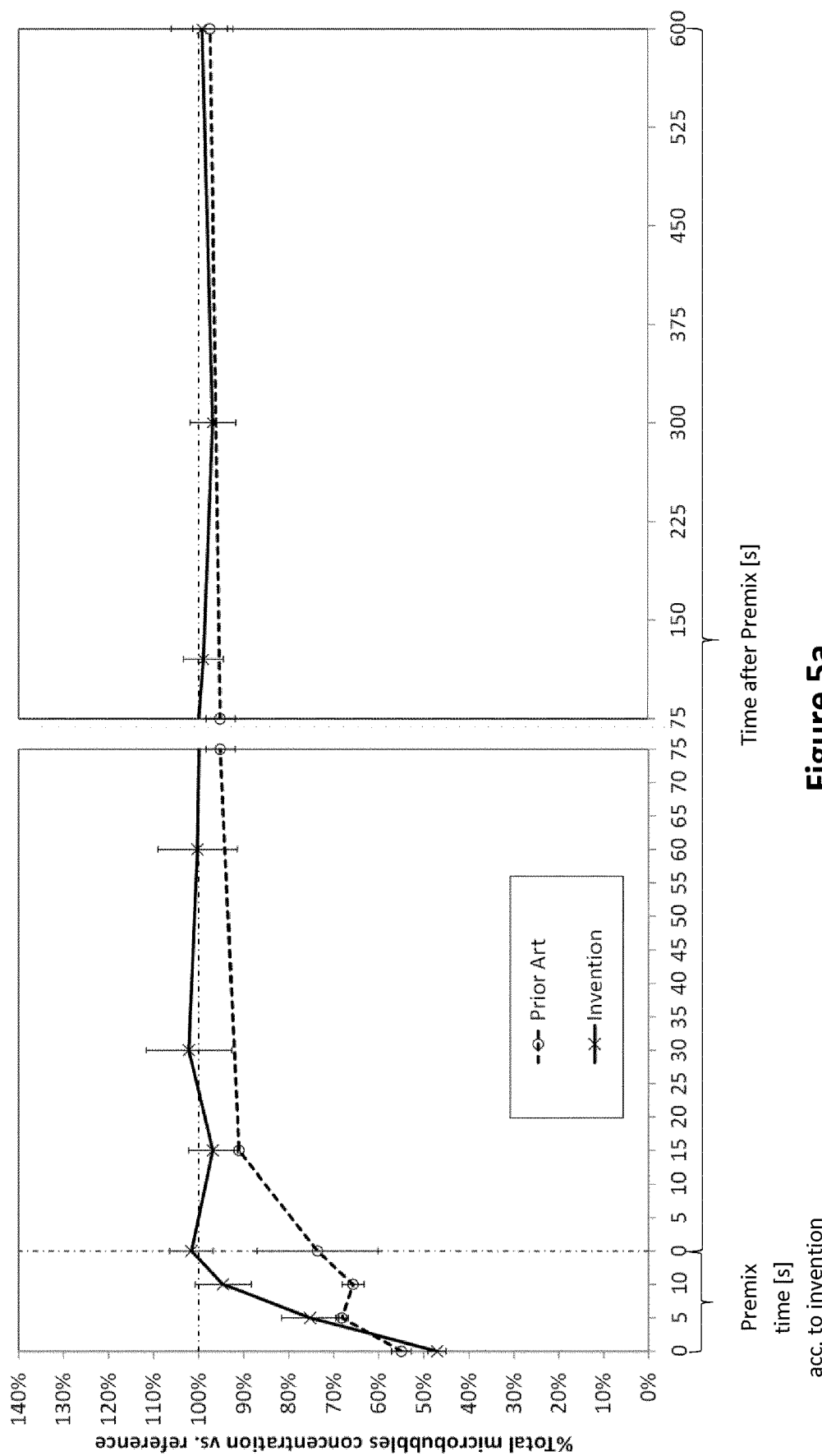
FIGS. 5a, 5b and 5c are graphs comparing a premixing step according to the present invention (said premixing step being followed by an infusion/injection and mixing step)
Figure 5B:
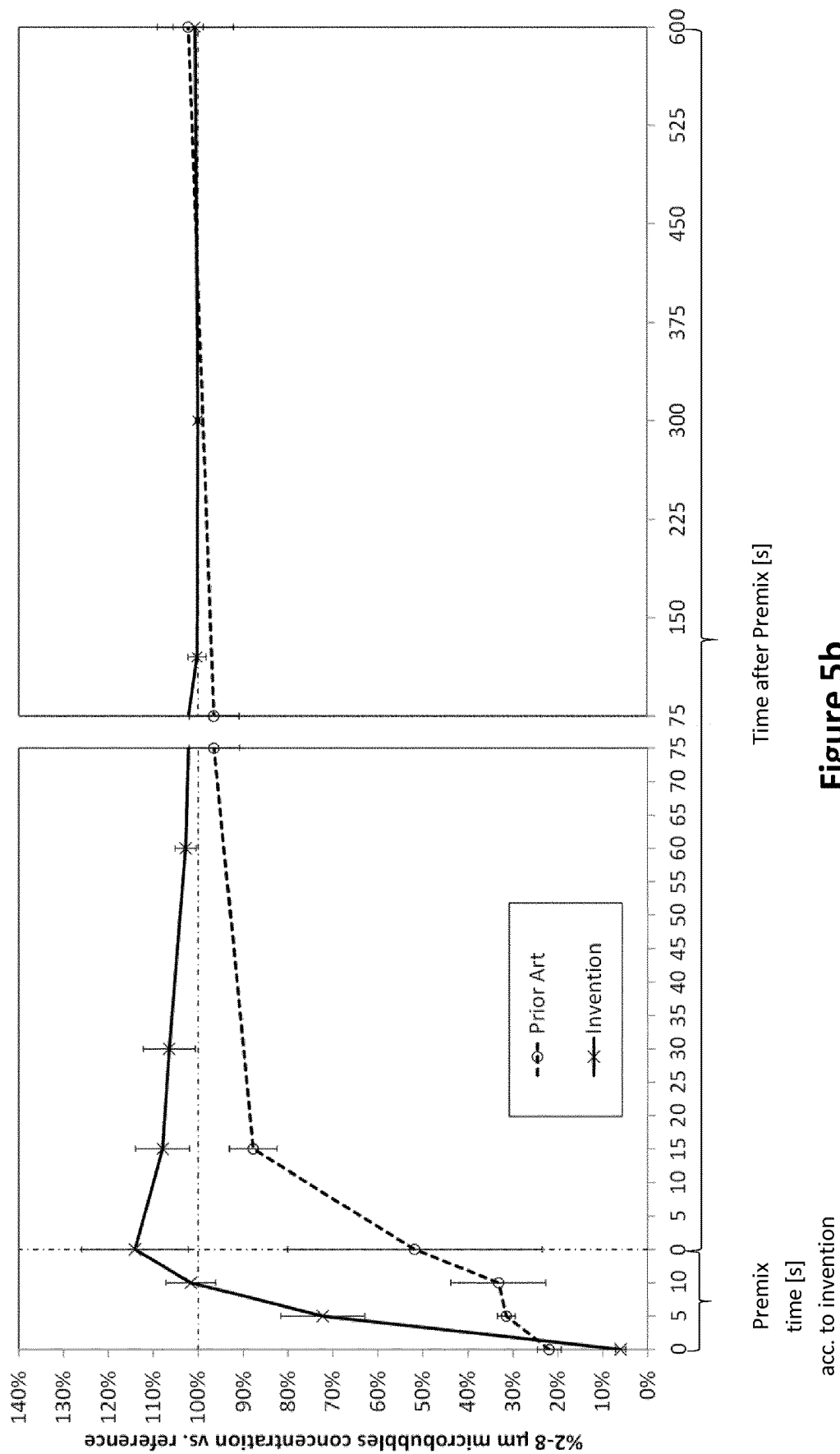
Figure 5C:
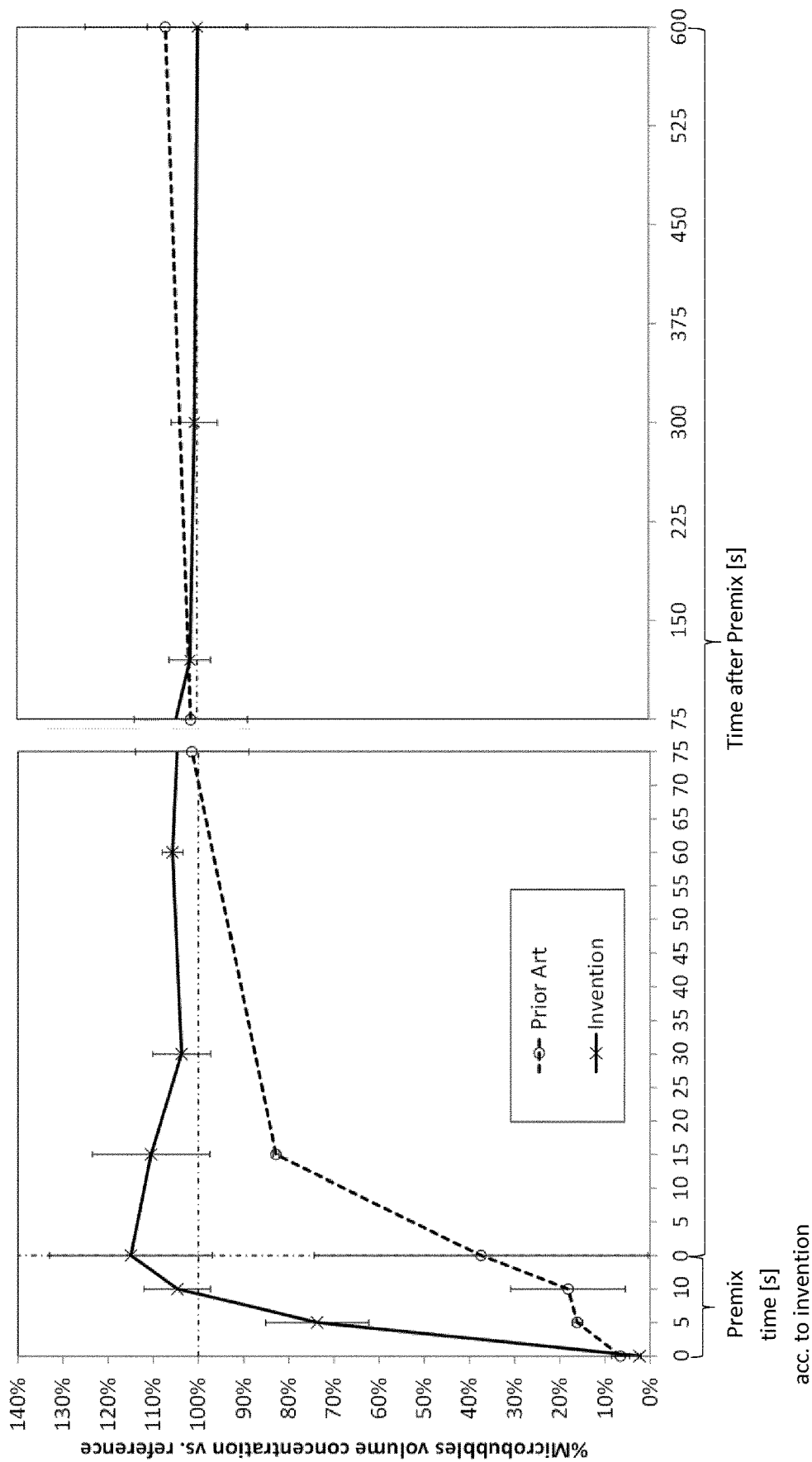

FIGS. 5a, 5b and 5c are graphs comparing the results obtained with a method according to the prior art and the results obtained with a method according to the present invention.

With first reference to FIG. 5a, it is evident that, according to the method of the prior art, an acceptable percentage of microbubbles concentration is obtained only after a time of about 90 seconds. Before this time, the percentage of microbubbles concentration is well lower 100%. In particular, after about 15 seconds, the percentage of microbubbles concentration is about 70%-75%.

On the contrary, according to the method of the present invention, a total percentage of microbubbles concentration higher than 100% is obtained at about 15 seconds and this concentration value is substantially maintained throughout the whole nominal infusion phase. The curve representing the method of the present invention is above the curve representing the method of the prior art during the whole nominal infusion phase. Therefore, the method according to the present invention results in a better performance in terms of total percentage of microbubbles concentration as well as in terms of reducing the duration time of the premixing phase before starting the infusion phase.

FIG. 5b is indicative of the percentage of 2 μm to 8 μm microbubble concentration with respect to the curve obtained with the method of the prior art.

In detail, the curve obtained according to the method of the prior art shows that, after a period of 15 seconds, the percentage of microbubbles having a size between 2 μm and 8 μm is around 50%. This percentage increases rather rapidly in the following 20 seconds and it reaches a value of about 90% at about 60 seconds. Then, the percentage increases slowly and it reaches a value close to 100% (but still under it) after a total time of about 90 seconds from the beginning of the initial mixing phase. During the nominal infusion phase, the percentage value is about 100%. Therefore, as said before, the duration time of the initial mixing phase before starting the infusion phase is too long and sometimes it is deemed to be not convenient for the operators.

On the contrary, according to the method of the present invention, the percentage of microbubbles having a size between 2 μm and 8 μm rapidly increases to a value higher than 100% after only 10 seconds. In 15 seconds from the start of the premixing phase, the percentage value is well above 100% (about 115%). Therefore, the nominal infusion phase can start earlier, e.g. after 10-15 seconds. After the premixing phase, the percentage of 2-8 μm microbubbles is maintained still higher than 100% for about 120 seconds and then it is stable around 100% for the remaining period of time (time duration) of the infusion phase.

FIG. 5c is indicative of the percentage of microbubbles volume concentration with respect to the curve obtained with the method of the prior art. The curves of the prior art method and of the method according to the invention are similar to the curves shown in FIG. 5b.

Therefore, it can be concluded that the complete sequential premixing phase according to the present invention (comprising the first premixing step and the second premixing step) demonstrated a very good re-homogenization of the contrast agent suspension during the premixing phase and very satisfying and stable contrast agent preservation profiles in terms of microbubbles concentration and size distribution during the whole infusion phase.

The invention claimed is:

1. A method of mixing a liquid composition, wherein said liquid composition comprises microparticles dispersed in a liquid carrier and wherein said liquid composition is contained in a syringe having a longitudinal horizontal axis (X-X), the method comprising:
    a first premixing step in which the syringe is oscillated about said longitudinal horizontal axis clockwise and counter-clockwise from a first reference point (B), through a first angle of rotation (δ) for a first period of time and at a first angular velocity;
    a second premixing step, performed in sequence to the first premixing step, in which the syringe is oscillated about said longitudinal horizontal axis clockwise and counter-clockwise from a second reference point (C; D), through a second angle of rotation (γ) for a second period of time and at a second angular velocity; and
    wherein said first angle of rotation is smaller than said second angle of rotation, and said first period of time is shorter than said second period of time.

2. The method of claim 1, wherein said second reference point (C) coincides with said first reference point (B).

3. The method of claim 1, wherein said second reference point (D) is different from said first reference point (B).

4. The method of claim 1, wherein said second angle of rotation (γ) is at least three times said first angle of rotation (δ).

5. The method of claim 1, wherein said first angle of rotation (δ) is between 20° and 60°.

6. The method of claim 1, wherein said second angle of rotation (γ) is between 90° and 160°.

7. The method of claim 1, wherein said first period of time is 1-3 seconds and said second period of time is 10-15 seconds.

8. The method of claim 1, wherein said first angular velocity is equal to said second angular velocity.

9. The method of claim 1, wherein said first angular velocity and second angular velocity are comprised between 800°/s and 2200°/s.

10. The method of claim 1, further comprising a combined injection/infusion and mixing step in which said liquid composition undergoes an injection/infusion phase while a mixing phase is carried out, wherein the syringe is oscillated about said longitudinal horizontal axis through a third angle of rotation and at a third angular velocity, the combined injection/infusion and mixing step being carried out after said second premixing step.

11. The method of claim 10, wherein the combined injection/infusion and mixing step is carried out immediately after said second premixing step.

12. The method of claim 10, wherein the injection/infusion phase of the combined injection/infusion and mixing step is started simultaneously to the mixing phase, or wherein the injection/infusion phase of the combined injection/infusion and mixing step is delayed with respect to the mixing phase.

13. The method of claim 1, wherein the first premixing step comprises a step of reversing the syringe by rotating the syringe about the longitudinal horizontal axis by about 180°.

14. The method of claim 1, wherein the first premixing step and the second premixing step each involve inversion of a syringe rotation direction between clockwise and counter-clockwise oscillation, and vice versa, and further comprising a pause step that is performed before each inversion of the syringe rotation direction occurring during the first and second premixing steps.

15. The method of claim 14, wherein the pause step comprises stopping the syringe rotation for a period of time of about 0.1 s.

16. The method of claim 1, wherein said liquid composition comprises an ultrasound contrast agent.

\* \* \* \* \*